(12) United States Patent
Dzwiniel et al.

(10) Patent No.: US 10,294,189 B2
(45) Date of Patent: May 21, 2019

(54) PROCESS FOR PRODUCING FLUORINATED ELECTROLYTE SOLVENT

(71) Applicants: Trevor L. Dzwiniel, Carol Stream, IL (US); Krzysztof Pupek, Plainfield, IL (US); Gregory K. Krumdick, Homer Glen, IL (US)

(72) Inventors: Trevor L. Dzwiniel, Carol Stream, IL (US); Krzysztof Pupek, Plainfield, IL (US); Gregory K. Krumdick, Homer Glen, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 15/270,256

(22) Filed: Sep. 20, 2016

(65) Prior Publication Data

US 2018/0079708 A1    Mar. 22, 2018

(51) Int. Cl.
*C07D 317/34* (2006.01)
*C07C 67/20* (2006.01)

(52) U.S. Cl.
CPC ............. *C07C 67/20* (2013.01); *C07D 317/34* (2013.01)

(58) Field of Classification Search
CPC .................................................... C07D 317/34
See application file for complete search history.

(56) References Cited

U.S. PATENT DOCUMENTS

2015/0050561 A1    2/2015  Zhang et al.
2015/0235772 A1*   8/2015  Koh ........................ H01G 9/035
                                                    429/332

FOREIGN PATENT DOCUMENTS

WO    WO-2004002985 A1 *  1/2004  ........... C07D 231/12

OTHER PUBLICATIONS

Material Safety Data Sheet. "Diglyme." (c) May 2011. Available from: < http://datasheets.scbt.com/sc-211330.pdf >.*

* cited by examiner

*Primary Examiner* — Noble E Jarrell
*Assistant Examiner* — John S Kenyon
(74) *Attorney, Agent, or Firm* — Cherskov Flaynik & Gurda, LLC

(57) ABSTRACT

The invention provides a method for producing halogenated carbonates, the method comprising reacting a halogenated alcohol or diol with a solid source of carbonyl moiety as a base in an ether.

14 Claims, 2 Drawing Sheets

PROCESS FOR PRODUCING FLUORINATED ELECTROLYTE SOLVENT

CONTRACTUAL ORIGIN OF THE INVENTION

The U.S. Government has rights in this invention pursuant to Contract No. DE-AC02-06CH11357 between the U.S. Department of Energy and UChicago Argonne, LLC, representing Argonne National Laboratory.

BACKGROUND OF THE INVENTION

1. Field of the Invention

This invention relates to electrolyte solvents and more specifically, this invention relates to a method for producing high voltage electrolyte solvents for batteries.

2. Background of the Invention

Carbon-fluorine bonds are among the strongest in organic chemistry, having an average bond energy of approximately 480 kJ/mol. As such, fluorinated organic compounds have high thermal, chemical, and electrochemical stability. It is this stability that makes such compounds preferred solvents for electrolytes used in high voltage batteries. Currently used electrolyte solvents do not perform well in high voltage lithium ion battery applications.

State of the art methods for making electrolyte solvents typically require severe reactants and reaction conditions. For example, in protocols for producing fluorinated carbonate solvents, phosgene and triphosgene are sometimes utilized. Other processes utilize hexachloroacetone to provide the carbonyl moiety. Chlorinated reagents are particularly troublesome inasmuch as chlorine wreaks havoc with battery chemistry. Therefore, elaborate distillation and purification steps are required to remove any traces of chlorine, and particularly chloride ions, from final electrolyte solvent produced.

The toxic reagents utilized in state of the art methods hinder commercialization. The methods are highly inefficient (30-40 percent yields) and require additional aqueous treatments to remove byproducts and residual reagents. This results in the generation of significant amounts of waste.

Prior art methods for producing the carbonated solvents often require internal temperatures of 100° C. maintained for 20 hours or more.

Furthermore, purification of fluorinated carbonate solvents is a difficult distillation, requiring a spinning column. This is because azeotropic mixtures may be formed between the formed solvent product and the aforementioned reaction solvents. (When azeotropic mixtures are boiled, the condensate has the same proportions of constituents as the pot mixture. As such, constituents cannot be separated via distillation.)

Also, state of the art methods for producing the electrolyte solvents often require strictly anhydrous reaction conditions. As such, nitrogen-filled gloveboxes are required. Overall, this results in a process that is too costly and too cumbersome to be commercially viable.

In light of the foregoing drawbacks, state of the art methods for producing electrolyte solvents often need to be conducted in controlled atmospheres (e.g., glove boxes). These processes typically require 8-12 hours for completion.

A need exists in the art for a method for economically producing electrolyte solvent, such as bis(trifluoroethyl) carbonate and trifluoropropylene carbonate, particularly for use in Li-ion battery electrolyte production. The method should use relatively mild reactants and require relatively low temperatures. The method should not require special reaction atmospheres. Also, the method should minimize waste streams. Lastly, the method should require no more than four hours, and preferably between about 1 and 4 hours.

SUMMARY OF INVENTION

An object of the invention is to provide a method for producing electrolyte solvent that overcomes many of the drawbacks of the prior art.

Another object of the invention is to provide a method for producing halogenated carbonate solvent, including, but not limited to fluorinated carbonate selected from the group consisting of bis(trifluoroethyl) carbonate, trifluoropropylene carbonate, bis(pentafluoropropyl) carbonate, and 4,5-bis (trifluoromethyl)-1,3-dioxolan-2-one. A feature of the invented method is its utilization of an ethereal reaction solvent, a halogenated alcohol and a nitrogen-containing carbonyl compound. An advantage of the invented method is that it takes between about 1 and about 4 hours to complete. Another advantage is that it occurs at ambient pressures (e.g., between about 800 and 1200 mbar) and at temperatures of between about 30° C. and about 70° C., preferably at temperatures between about 45° C. and about 60° C.

Yet another object of the present invention is to provide a method for producing bis(trifluoroethyl) carbonate. A feature of the method is the use of methyl tert-butyl ether and 1,1 carbonyldiimidazole as the solvent and carbonyl source, respectively. An advantage of the invented method is that it utilizes a heterogeneous (i.e. solid phase) carbonyl source, therefore simplifying filtration and purification steps.

Still another object of the present invention is to provide a process for producing halogenated carbonates. A feature of the invention is reacting a halogenated hydroxyl moiety with a solid phase, carbonyl compound in the presence of a liquid solvent. An advantage of the invention is that a 75 percent yield is realized with a 99 percent purity after just a single distillation step. Reaction byproducts are isolated with a single filtration step. Another advantage is that the protocol is chlorine free.

Briefly, the invention provides a method for producing halogenated carbonates, the method comprising reacting a halogenated alcohol with a solid source of carbonyl moiety and in an ether as a reaction solvent. A boiling point of the ether determines a boiling point of the reaction liquor. The ether may be a below 75° C. boiling point compound selected from the group consisting of methyl tert-butyl ether, diethyl ether, tetrahydrofuran, and combinations thereof.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
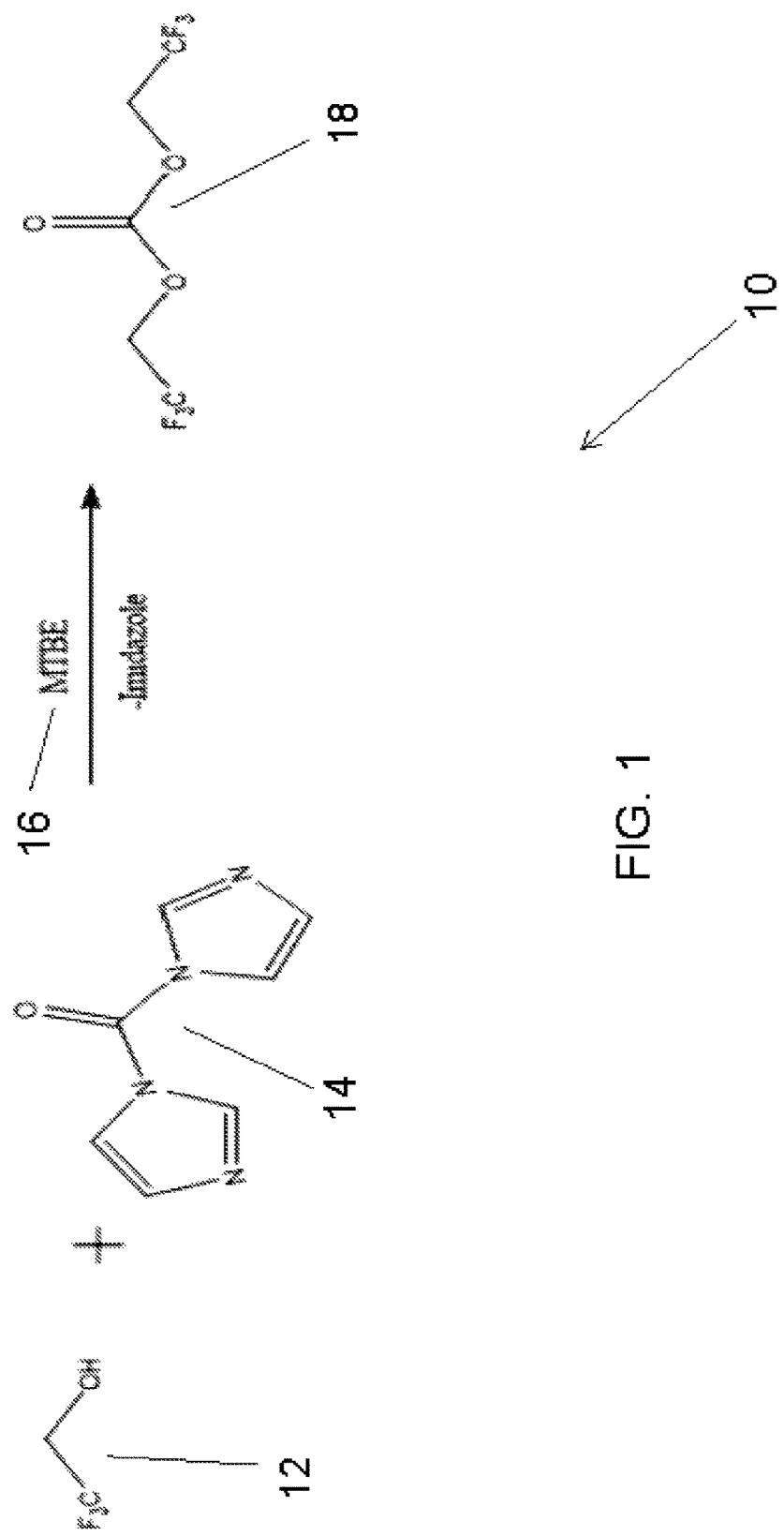
FIG. 1 is a chemical reaction sequence for producing bis(trifluoroethyl) carbonate, in accordance with features of the present invention.

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Halogenated carbonates, and particularly fluorinated carbonates, are a family of solvents that show promise in high voltage battery prototypes. In a preferred embodiment of the instant protocol wherein bis(trifluoroethyl) carbonate is produced, trifluoroethanol is the substrate providing the trifluoroethyl group. However, other fluorinated alcohols and be used as suitable substrates to produce different solvent structures. It is noteworthy that prior art processes do not utilize fluorinated alcohols. Also, unlike prior art protocols, the instant method does not require strong base, such as KOH.

The invention provides a process for generating halogenated carbonates using common solvents and carbonyl sources. The invented system is more reactive toward carbonyldiimidazole and does not need the base to start the reaction.

An embodiment of the invention provides a process for producing bis(trifluoroethyl) carbonate for use as a high voltage electrolyte solvent for lithium ion batteries. (See FIG. 1.) The process is also utilized to produce trifluoropropylene carbonate. (See FIG. 2) The process can be conducted at ambient pressure.

When one liter quantities of the target solvent are required, the invention allows for a rapid filtration and distillation step to generate yields higher than 60 percent, and purities greater than 99 percent. For example, purity of the halogenated carbonates is greater than about 99.5 percent after a single distillation step. Room temperature, normal paper, cloth or glass- or metal-frit filters are suitable for filtering out the solid byproduct. A standard vacuum filtration paradigm, wherein a pump imparts negative pressure (e.g., suction) to the downstream surface of the filter media, can be utilized to increase the speed of the filtration step.

A salient feature of the invented method is the elimination of any aqueous wash steps. As such, the invented process requires no aqueous wash step. The product is purified without an aqueous extraction step.

FIG. 1 depicts a reaction sequence for the invented process, the sequence designated therein as numeral 10. A triple halogenated ethanol 12 is combined with carbonyldiimidazole 14 in the presence of methyl tertbutyl ether (MTBE) 16. The hydroxyl group on the alcohol reacts with the carbonyl group on the CDI. The intermediate, trifluorethyl-C=O-imidazole generated subsequently reacts with oxygen of a second hydroxyl group on a second alcohol. A fluorinated product 18 produced is bis (2,2,2-trifluoroethyl) carbonate (designated throughout this specification as F-DEC).

Figure 2:
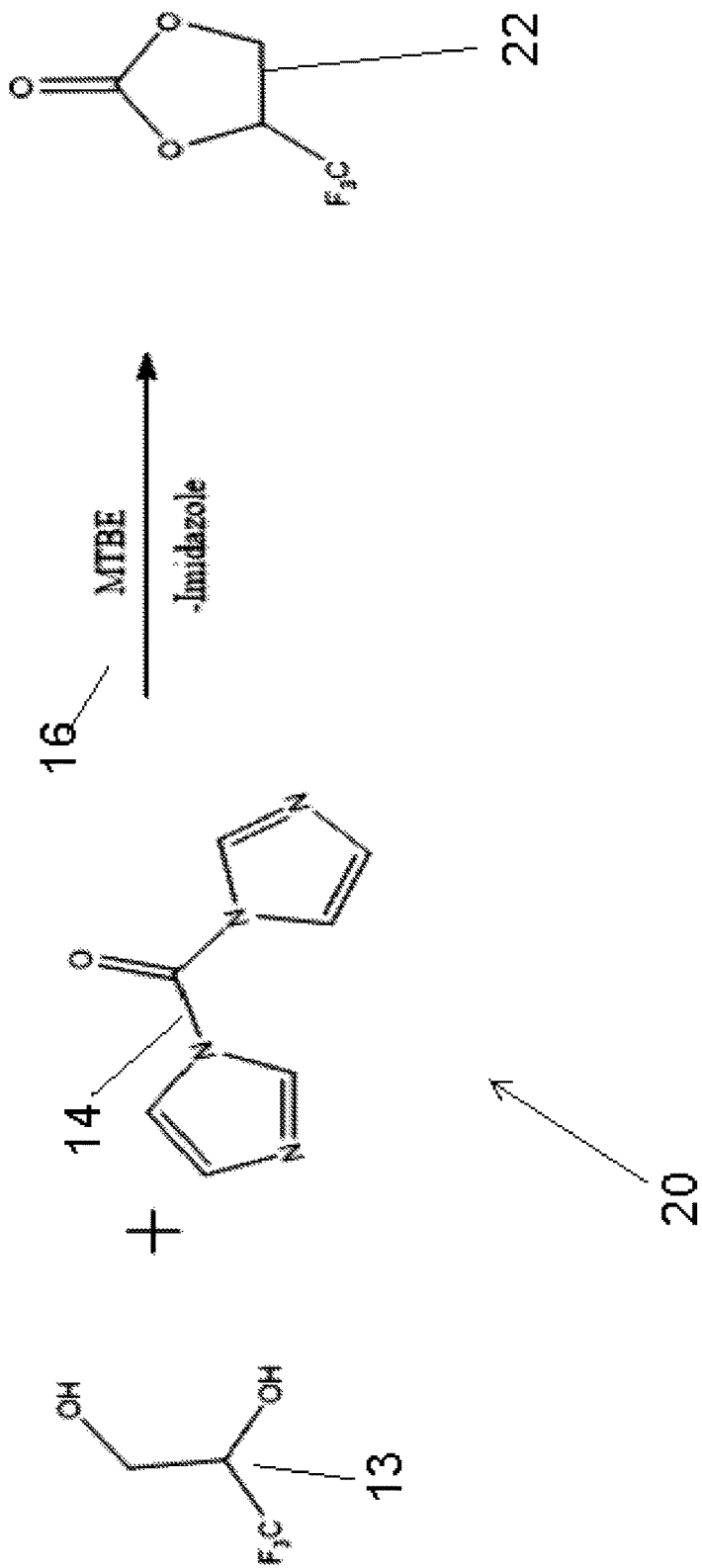
FIG. 2 is a chemical reaction sequence for producing trifluoropropylene carbonate, in accordance with features of the present invention.

FIG. 2 depicts a reaction mechanism, designated as numeral 20, for producing trifluorpropylene 22. Trifluoropropylene glycol 13, is combined with carbonyldiimidazole 14 in the presence of methyl tertbutyl ether (MTBE) 16. As above, the hydroxyl group on the alcohol reacts with the carbonyl group on the CDI.

A myriad of halogenated hydroxyl moieties are suitable for the protocol. For example, fluorine containing compounds selected from the group consisting of trifluoroethanol, 1,1,3,3,3-hexafluoro-2-propanol, 2,2,3,3,3-pentafluoropropanol, 2,2,3,3,4,4,4-heptafluoro-1-butanol, 2,2-difluoroethanol, 2,2,3,3-tetrafluoro-1,4-butanediol, and combinations thereof will suffice.

Generally, the solid carbonyl source can be a nitrogen containing compound selected from the group consisting of carbonyldiimidazole, disuccinimidyl carbonate, 1,1'-Carbonyl-di-(1,2,4-triazole), and combinations thereof.

Solid byproducts are removed via simple filtration. No aqueous wash is required. The invented process embodies a heterogeneous reaction in that a liquid solvent is combined with a solid source of carbonyl moiety. The resulting filter cake is washed with MTBE to remove product entrained in the cake. Residual MTBE is distilled and recovered, for reuse. Water is not required but and in fact its use would add extra separation and drying steps. Also, any water wash is not reuseable. However, instances where MTBE is not to be recovered, a water wash may be utilized.

The invented process replaces homogeneous reaction protocols. Specifically, the invented process eliminates the need for anhydrous solvents and liquid amine bases (such as pyridine and triethyl amine).

Reagents such as the tri-fluorinated ethanol can be modified to present fewer or more fluorines on the final product. Suitable hydroxyl-containing compounds include any carbon chain of five carbons or less, either partially or completely fluorinated. Given that the instant protocol eliminates the potential of chloride ions forming (and therefore damaging lithium ion chemistry) the compounds may be partially substituted with chlorine as well. Suitable hydroxyl-containing compounds include, but are not limited to trifluoroethanol, 1,1,3,3,3-hexafluoro-2-propanol, 2,2,3,3,3-pentafluoropropanol, 2,2,3,3,4,4,4-heptafluoro-1-butanol, 2,2-difluoroethanol, 2,2,3,3-tetrafluoro-1,4-butanediol, and combinations thereof.

In light of the foregoing, potential fluorinated solvents produced by the invented process are represented by the following generic Formula I and Formula II

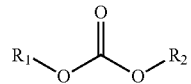

Formula I

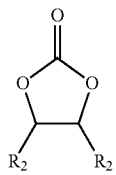

Formula II wherein R1 and R2 are individually an alkyl or $C_nH_xF_y$ group, an H, F, and combinations thereof, wherein each x is individually from 0 to 2n, each y is individually from 1 to 2n+1, and each n is individually an integer from 1 to 5.

EXAMPLE 1

Trifluoroethanol is added slowly to a warm (45-60 and preferably 50-55 C) suspension of 1,1'carbonyldiimidazole in MTBE. After the reaction is complete and the reaction liquor cooled, any imidazole solids are filtered away. Solvent is removed by distillation and the product is fractionally distilled.

A reactor equipped with drain valve, internal temperature probe, addition port, condenser, and gas inlet/outlet adapters was flushed with nitrogen. The jacket of the reactor was connected to a heating/chilling circulator. The gas outlet port was connected to a silicon oil bubbler.

The reactor was charged with 2,2,2-trifluoroethanol. The liquid was stirred and heated under an inert atmosphere (e.g. a nitrogen blanket) to approximately 55° C. A solid carbonyl source (e.g., carbonyldiimidazole) was added in portions over 45 minutes. The stirring speed was adjusted from 200-270 rpm to keep good mixing. The jacket temperature generally was about 40C and below 55 C and preferably between about 46 and about 48° C. throughout the addition.

As the reaction progressed, a thin stir-able suspension began to form from the yellow/brown solution, starting about % through the addition. The temperature was increased to about 60° C., then to about 68° C. to completely dissolve all solids. After 3 h at 68° C., the mixture was cooled to 50° C. and imidazole crystallization induced by seeding lightly. A clean pipet was dipped into the solution and removed. Upon cooling, imidazole crystallized on the tip. When the tip was placed back into the reaction mixture, crystallization of the mixture was induced. The mixture was cooled to 30° C., and water was added. The reaction temperature rapidly dropped to 9° C., and two liquid phases formed. The top layer (aqueous) was dark brown, the bottom layer was clear and colorless.

The top aqueous phase was removed by peristaltic pump as much as practical. An additional charge of water was made, and mixed well to remove a small plug on the bottom of the reactor. The bottom organic layer was then drained into a separatory funnel and washed with dilute acid (e.g. 5 percent HCl.) The organic layer was the separated and dried over magnesium sulfate (5.8 g), left overnight, and filtered into a distillation pot.

The product was fractionally distilled at 38-40 torr, and had a boiling point of about 46° C. Fractions were analyzed by GC/MS prior to combining.

EXAMPLE 2

A glass reactor equipped with drain valve, internal temperature probe, addition port, condenser, and gas inlet/outlet adapters was flushed with nitrogen. The jacket of the reactor was connected to a heating/chilling circulator. The gas outlet port was connected to a silicon oil bubbler.

The reactor was charged with CDI and MTBE and heated to about 50° C. A solution of trifluoropropylene glycol was added at 2-3 ml/min. The reactor was maintained at about 50° C. overnight, then cooled to about 5° C. over about 3 hours. At 36° C., the solution was seeded by withdrawing 1 ml and rapidly cooling to form solid imidazole. This cooled suspension was returned to the reactor. Imidazole immediately began to crystallize in the reactor. Once cooled completely, the supernatant liquid was removed. The solids were washed with 1:1 MTBE:heptane. These solutions were then separately roto-vaped to a thin oil. GC analysis concluded they were the same composition (wrt imidazole concentration) and they were then combined. The next day, this was distilled. Given a starting substrate of about 200 grams of the trifluoropropylene glycol, and about 260 grams CDI, product yield was about 175 g.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those having skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods. As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A method for producing a halogenated carbonate selected from the group consisting of bis(2,2,2-trifluoroethyl) carbonate, trifluoropropylene carbonate, bis(pentafluoropropyl) carbonate, 4,5-bis(trifluoromethyl)-1,3-dioxolan-2-one, and combinations thereof, the method comprising:
reacting a fluorinated hydroxyl moiety selected from the group consisting of trifluoroethanol, 1,1,3,3,3-hexafluoro-2-propanol, 2,2,3,3,3pentafluoropropanol, 2,2,3,3,4,4,4-heptafluoro-1-butanol, 2,2-difluoroethanol, 2,2,3,3-tetrafluoro-1,4-butanediol, and combinations thereof, with a solid carbonyl source in an ether to create a reaction mixture, wherein the reaction mixture of the fluorinated hydroxyl moiety and the solid carbonyl source comprises a heterogeneous reaction liquor, and wherein no chlorinated compounds are utilized;
wherein the ether is a below 75 C boiling point compound selected from the group consisting of methyl tert-butyl ether, diethyl ether, tetrahydrofuran, and combinations thereof;
wherein the solid carbonyl source is a nitrogen-containing compound selected from the group consisting of carbonyldiimidazole, disuccinimidyl carbonate, 1,1'-Carbonyl-di(1, 2,4-triazole), and combinations thereof.

2. The method as recited in claim 1 wherein a boiling point of the ether determines a boiling point of the reaction liquor.

3. The method as recited in claim 1 wherein the method occurs in ambient pressure.

4. The method as recited in claim 1 wherein halogenated carbonates are produced in about 1 to about 4 hours.

5. The method as recited in claim 1 wherein the halogenated carbonates are produced at temperatures between about 30° C. and about 70° C.

6. The method as recited in claim 1 wherein purity of the halogenated carbonates is greater than about 99.5 percent after a single distillation step.

7. The method as recited in claim 1 wherein the product is purified without an aqueous extraction step.

8. The method as recited in claim 1 wherein reaction byproducts are isolated with a single filtration step.

9. A method for producing fluorinated carbonates having the following Formula I

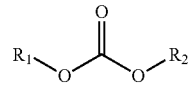

or Formula II

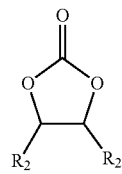

wherein $R_1$ and $R_2$ are a fluorine-containing $C_nH_xF_y$ group and wherein each x is individually from 0 to 2n, each y is individually from 1 to 2n+1, and each n is individually an integer from 1 to 5, the method comprising reacting a liquid fluorinated hydroxyl moiety of five carbons or less with a nitrogen containing solid carbonyl source in an ether having a boiling point below 75° C. to create a reaction mixture, wherein the reaction mixture of the halogenated hydroxyl moiety and the solid carbonyl source comprises a heterogeneous reaction liquor, and wherein no chlorinated compounds are utilized;
wherein the fluorinated hydroxyl moiety is a fluorinated hydroxyl compound selected from the group consisting of trifluoroethanol, 1,1,3,3,3-hexafluoro-2-propanol, 2,2,3,3,3-pentafluoropropanol, 2,2,3,3,4,4,4-heptafluoro-1-butanol, 2,2-difluoroethanol, 2,2,3,3-tetrafluoro-1,4-butanediol and combinations thereof;
and wherein the nitrogen containing solid carbonyl source is a nitrogen containing solid carbonyl source selected from the group consisting of carbonyldiimidazole, disuccinimidyl carbonate, 1,1'-Carbonyl-di-(1,2,4-triazole), and combinations thereof.

10. The method as recited in claim 1 wherein the ether is methyl tert-butyl ether.

11. The method as recited in claim 1 wherein the solid carbonyl source is carbonyldiimidazole.

12. The method as recited in claim 1 wherein the halogenated carbonate is bis(2,2,2-trifluoroethyl) carbonate.

13. A method for producing fluorinated carbonates, the method comprising: reacting trifluoroethanol with carbonyldiimidazole in methyl tert-butyl ether to create a reaction mixture, wherein the reaction mixture comprises a heterogeneous reaction liquor.

14. The method as recited in claim 13 wherein the fluorinated carbonate is bis-(2,2,2-trifluoroethyl) carbonate.

* * * * *